(12) United States Patent
Li et al.

(10) Patent No.: US 9,266,084 B2
(45) Date of Patent: Feb. 23, 2016

(54) AUTOMATIC SYNTHESIZER APPARATUS FOR PRODUCING RADIOPHARMACEUTICAL TUMOR IMAGING AGENT GALLIUM-68-DOTATATE AND METHOD THEREOF

(71) Applicants: Ming-Hsin Li, Taoyuan County (TW); Hsin-Han Hsieh, Taoyuan County (TW)

(72) Inventors: Ming-Hsin Li, Taoyuan County (TW); Hsin-Han Hsieh, Taoyuan County (TW)

(73) Assignee: INSTITUTE OF NUCLEAR ENERGY RESEARCH, Taoyuan (TW)

( * ) Notice: Subject to any disclaimer, the term of this patent is extended or adjusted under 35 U.S.C. 154(b) by 266 days.

(21) Appl. No.: 13/916,599

(22) Filed: Jun. 13, 2013

(65) Prior Publication Data

US 2014/0369928 A1    Dec. 18, 2014

(51) Int. Cl.
| | |
|---|---|
| *A61K 51/00* | (2006.01) |
| *A61M 36/14* | (2006.01) |
| *B01J 19/00* | (2006.01) |
| *A61K 51/08* | (2006.01) |
| *C07B 59/00* | (2006.01) |

(52) U.S. Cl.
CPC ........... *B01J 19/0053* (2013.01); *A61K 51/083* (2013.01); *C07B 59/00* (2013.01)

(58) Field of Classification Search
CPC .... B01J 19/0053; C07B 59/00; A61K 51/083
See application file for complete search history.

(56) References Cited

U.S. PATENT DOCUMENTS

2007/0031329 A1 *   2/2007   Velikyan et al. ............. 424/1.49

FOREIGN PATENT DOCUMENTS

WO     WO 2010021719 A1 *   2/2010

OTHER PUBLICATIONS

Dicristoforo et al. Nucl. Med. Comm. 2007, 28:870-875.*
Petrik et al. Nucl. Med. Comm. 2011, 32:887-895.*

* cited by examiner

*Primary Examiner* — Michael G Hartley
*Assistant Examiner* — Sean R Donohue

(57) ABSTRACT

The invention provides an automatic synthesizer apparatus and method for producing radiopharmaceutical tumor imaging agent Gallium-68-DOTATATE with one button control process to effectively isolate the medication in vials from the contamination of environment and manual operations, saving the costs of investment in production with alleviation of the critical standard required for the environmental equipments to be used for production.

4 Claims, 6 Drawing Sheets

AUTOMATIC SYNTHESIZER APPARATUS FOR PRODUCING RADIOPHARMACEUTICAL TUMOR IMAGING AGENT GALLIUM-68-DOTATATE AND METHOD THEREOF

BACKGROUND OF THE INVENTION

1. Field of the Invention

The invention relates to an automatic synthesizer apparatus and method for producing radiopharmaceutical tumor imaging agent Gallium-68-DOTATATE (1,4,7,10-tetraazacyclododecane-1,4,7,10-tetraacetic acid octreotate), and more particularly to an automatic synthesizer apparatus having convenient control process for saving cost with increasing yield.

2. Description of Related Art

Gallium isotopes Ga-68 are feasible to form stable complex with DOTA without difficulty, this complex with a high ratio of activity can be used to locate peptides or other small molecules. Gallium-68 after completely transformed yields can be as high as 89% suitable for PET imaging. Since Ga-68 nuclide has half-life of 68 minutes, which is suitable for pharmacokinetics assessment for many kinds of peptides, and this feature of Ga-68 nuclides is well used in the fields of diagnostic imaging and therapeutic research.

Conventional operational process for producing radiopharmaceutical tumor imaging agent Gallium-68-DOTATATE generally includes hardware and software two parts. In the part of hardware, conventional synthesizing box has shortcomings in the aspect of automatic labeling process, construction, layout, and arrangement that need to be resolved. In the part of software, the automatic labeling process of conventional synthesizing box is attached to and controlled by other equipments, causing problems of complexity in the process of operation and with its bulk software. As a consequence, the production yield would be low and resources would be wasted were the problems not resolved.

In the prior art EP2488212/WO201133120A2, it developed a set of new labeling method for radioactive material. The prior art disclosed a method of obtaining $^{68}$Ga from a $^{68}$Ge/$^{68}$Ga radioisotope generator and a method of preparing $^{68}$Ga-radiolabelled complexes using the obtained $^{68}$Ga that comprise elution of the generator with an aqueous chloride ion solution and an apparatus for carrying out the $^{68}$Ga metal complex formation. Nevertheless, the hardware has shortcomings in the aspect of process, construction, layout and arrangement. It needs to be solved to avoid yield decreasing and resources wasting.

In the prior art EP2467365/WO2011020907, it disclosed a method of labeling biological targeting molecules (BTMs) of interest with radioiodine, preparing radioiodine BTMs and radiopharmaceutical compositions, and of vivo imaging processing. Since the software is loaded in and controlled by other equipments, a large number of data and program are built in chips, causing complexity in manipulation and high failure rate. Therefore, it is important to solve the problems of manipulation complexity and bulk software involved to avoid yield decreasing and resources wasting.

To overcome the drawbacks, the present invention tends to provide an automatic synthesizer apparatus for producing radiopharmaceutical tumor imaging agent Gallium-68-DOTATATE and method to mitigate and obviate the aforementioned problems.

SUMMARY OF THE INVENTION

The primary objective of the present invention is to provide an automatic synthesizer apparatus for producing radiopharmaceutical tumor imaging agent Gallium-68-DOTATATE with downscale software program in the operation process to minimize its failure rate.

Another objective of the invention provides an automatic synthesizer apparatus and method for producing radiopharmaceutical tumor imaging agent Gallium-68-DOTATATE with one button control process to effectively isolate the medication in vials from environment contamination and manual operations for saving cost of investment for contamination free production.

Another objective of the invention is to provide an automatic synthesizer apparatus and method that allows the use of a plurality of reagent vials containing reagents required in the process, a plurality of collection vials for receiving solutions after reaction or purification in the process and the final product of Gallium-68-DOTATATE dissolved in absolute ethanol by means of a programmable process to control the output of each reagent vial and the reception of each collection vial to produce the product of Gallium-68-DOTATATE with high yield and without contamination.

Another objective of the invention is to provide an automatic synthesizer apparatus and method that allows the process for producing Gallium-68-DOTATATE in four stages including injection of solution, oxidation reaction, interruption and neutralization, filtration and collection. The apparatuses used in the present invention comprise each unit module being configured and controlled by software program for the completion of these four stages in an automatic operation.

Another objective of the invention is to provide an automatic synthesizer apparatus and method that allows the production of Gallium-68-DOTATATE simply by placing reaction medicines in specified vials, turning on power and starting the operation system. The medication preparation can be completed in a short period of time to provide in-time clinical diagnostic use.

The automatic synthesizer apparatus for producing radiopharmaceutical tumor imaging agent Gallium-68-DOTATATE of the present invention can be exploited in the development of radiopharmaceutical for PET, and the technology can be extended to related diagnostic applications with tumor imaging agent. The technology of present invention is also applicable to the related industries of radiopharmaceutical development and manufacturing.

DETAILED DESCRIPTION OF THE PREFERRED EMBODIMENT

Figure 1:
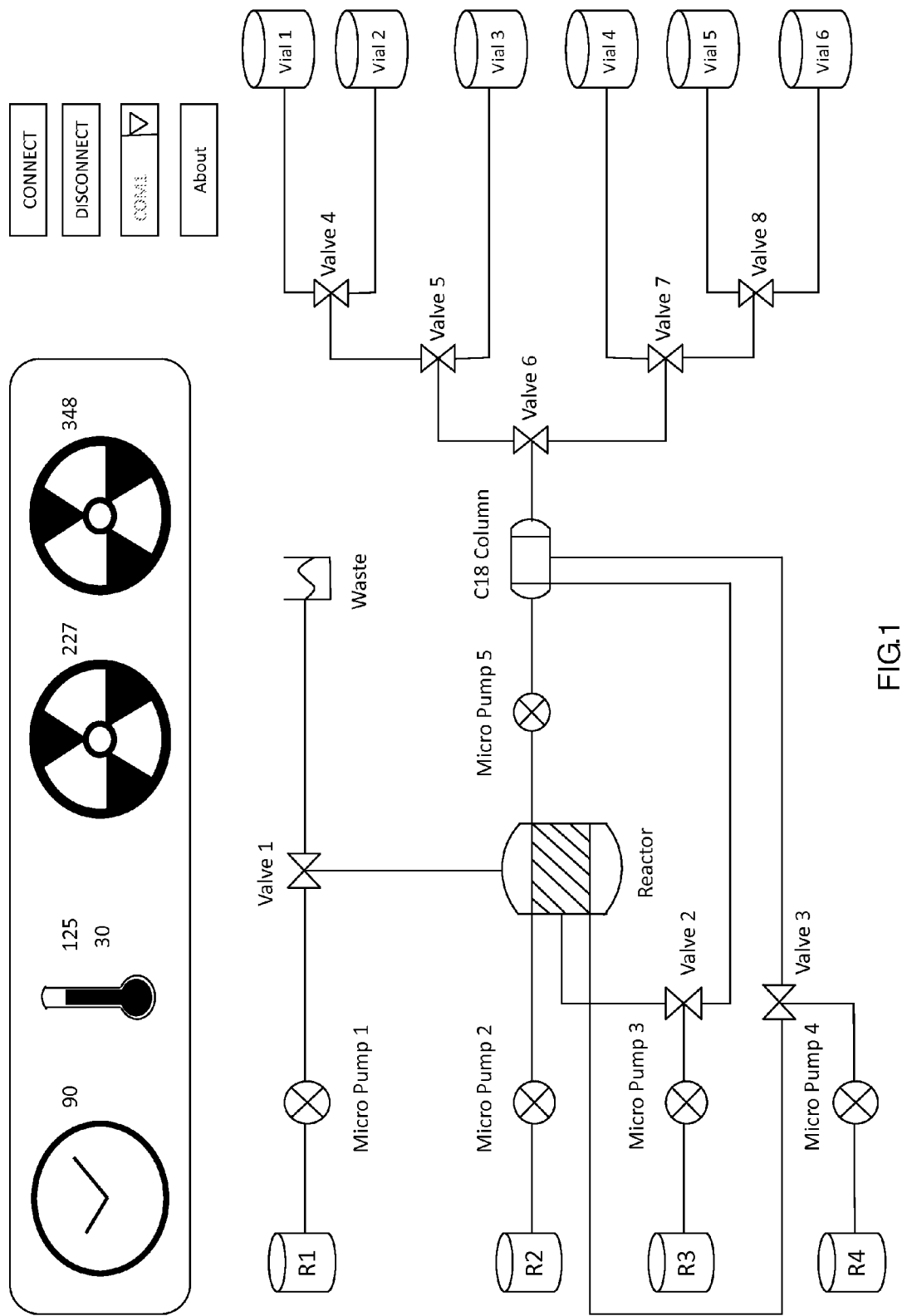
FIG. 1 is a computerized operational interface diagram of the automatic synthesizer apparatus of the present invention for producing radiopharmaceutical tumor imaging agent Gallium-68-DOTATATE.

FIG. 1 is a computerized operational interface diagram of the automatic synthesizer apparatus of the present invention for producing radiopharmaceutical tumor imaging agent Gallium-68-DOTATATE. The system started with initiating program in computer for the selection of connection port between the computer and the apparatus of the present invention, and followed by pressing the connection button on the operational panel of the apparatus. When the operation process completed, the program is ended and a record file output.txt will be generated by the system for recording values of time, humidity and sensors, which can be initiated for output to work for the system.

Figure 2:
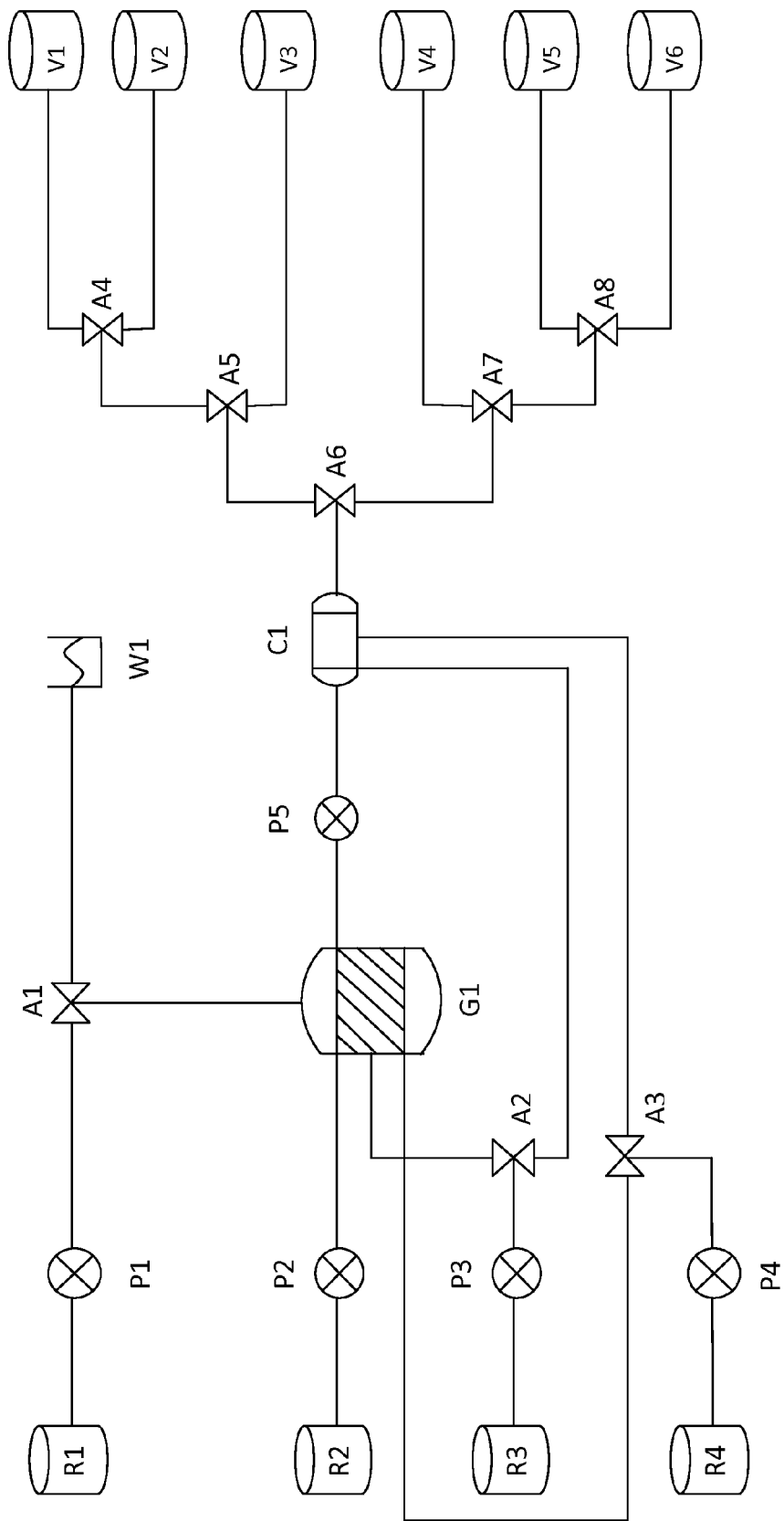
FIG. 2 is a schematic diagram of the automatic synthesizer apparatus of the present invention for producing radiopharmaceutical tumor imaging agent Gallium-68-DOTATATE.

FIG. 2 is a schematic diagram of the automatic synthesizer apparatus of the present invention for producing radiopharmaceutical tumor imaging agent Gallium-68-DOTATATE. In the FIG. 2, R1-R4 denote reagent vials, of which the first reagent vial R1 filled with 0.6M or 0.1M hydrochloride 4 mL with gallium-68 nuclides; the second reagent vial R2 filled with sodium acetate 2.5M 1.5 ml, the third reagent vial R3 filled with a DOTATATE solution 50 μl or deionized water (DI water) 8 ml alternatively; the fourth reagent vial R4 filled with absolute ethanol 1.1 ml; V1-V5 denote collection vials, and V6 denotes a reserve collection vial, of which the first collection vial V1 contains solution of hydrochloride, acetate sodium and DOTATATE with gallium-68 nuclide obtained through reaction in the Gallium-68-DOTATATE reactor G1 and purification in the C-18 reversed chromatography column (C-18 RPC) C1; the second collection vial V2 contains DI water eluent through the Gallium-68-DOTATATE reactor G1 and the C-18 reversed chromatography column C1; the third collection vial V3 contains DI water eluent directly through the C-18 reversed chromatography column C1; the fourth collection vial V4 contains absolute ethanol eluent; and the fifth collection vial V5 contains solution of Gallium-68-DOTATATE dissolved in absolute ethanol.

In the FIG. 2, A1-A8 denote solenoid valves for process control, of which the first solenoid valve A1 controls flow of the gallium-68 radioactive solution in the first reagent vial R1 in or out of the vial, if the impurity is high or the gallium-68 radioactive solution is in excess, the first solenoid valve A1 will let the solution flow to waste vial W1; the second solenoid valve A2 controls flow of the DI water into the GA-68-DOTATATE reactor G1 and the C-18 reversed phase chromatography column C1 the third solenoid valve A3 controls flow of the absolute ethanol into the GA-68-DOTATATE reactor G1 and the C-18 reversed phase chromatography column C1, the fourth solenoid valve A4 controls flow of hydrochloric acid, sodium acetate and DOTATATE with gallium-68 nuclide after being mixed and heated in the GA-68-DOTATATE reactor G1 and passing through C-18 reversed phase chromatography column C1 before being collected in the first collection vial V1, and controls flow of the DI water eluent into the second collection vial V2; the fifth solenoid valve A5 control flow of the DI water eluent into the third collection vial V3; the sixth solenoid valve A6 controls flow of solution after passing through C-18 reversed phase chromatography column C1 to the fifth solenoid valve A5 or the seventh solenoid valve A7; the seventh solenoid valve A7 controls flow of the absolute ethanol eluent into the fourth collection vial V4 and through the eighth solenoid valve A8 into the fifth collect vials V5; the eighth A8 solenoid valve controls flow of absolute ethanol eluent to the fifth collect vials V5 or into the reserve vial V6;

The details of the operation process will be described in the FIG. 3. By use of the software program, the process control of the present invention only needs to press "CONNECT" button or "DISCONNECT" button, simplifying the process control and solving problems encountered with bulk software programs in the conventional equipment.

Figure 3:
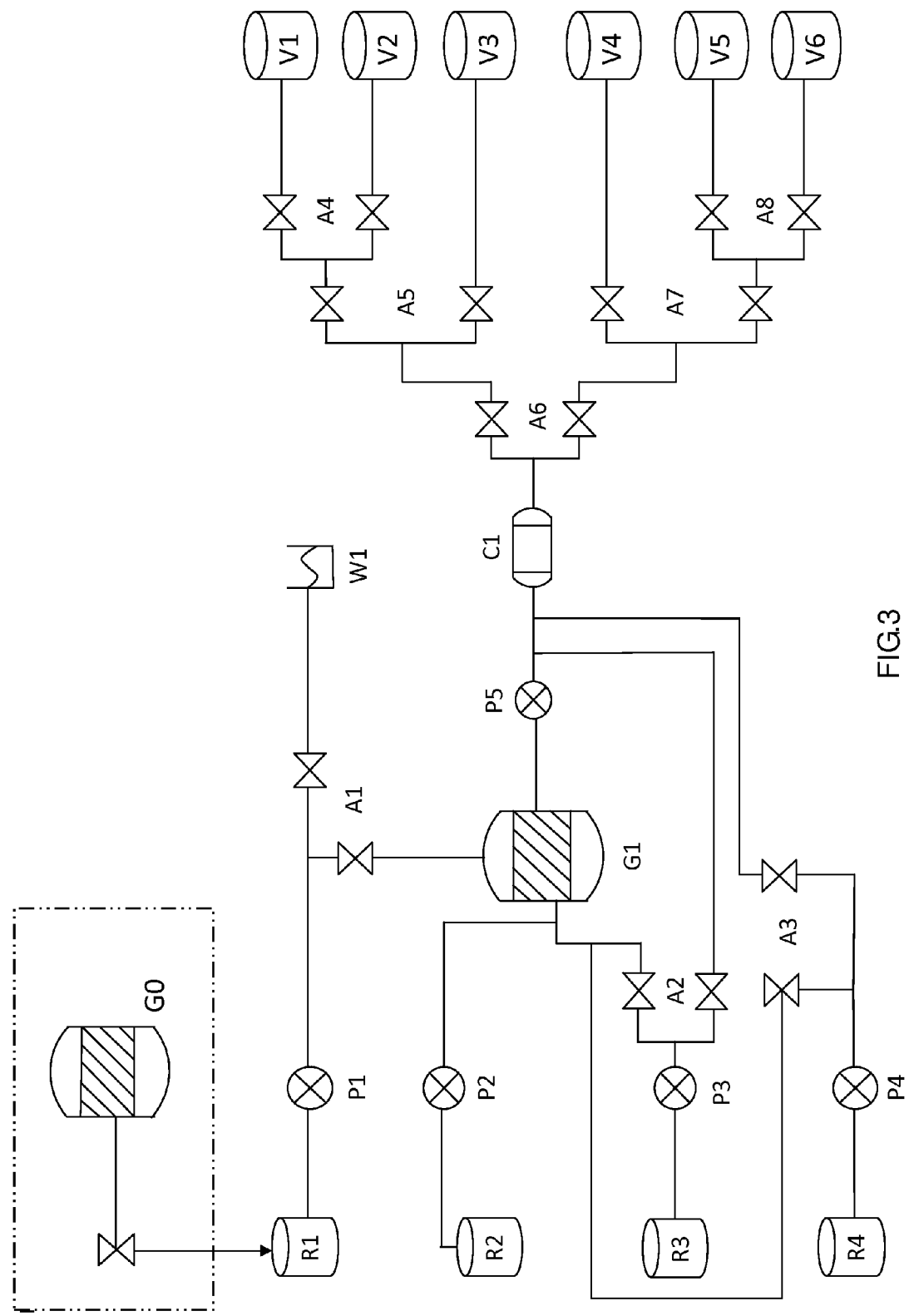
FIG. 3 is a logic diagram of the automatic synthesizer apparatus of the present invention for producing radiopharmaceutical tumor imaging agent Gallium-68-DOTATATE.

In the FIG. 3, the logic diagram of the automatic synthesizer apparatus of the present invention is described in four stages, excluding the portion of prior art within the dotted area.

(1) From first reagent vial R1: With the first micro pump P1, the GA-68 containing 0.6M or 0.1M hydrochloride eluent 4 ml is used for washing Tin dioxide or Titanium dioxide contained in the generator G0, and conveying the product thus obtained into the GA-68-DOTATATE reactor G1, and the redundant hydrochloride will be fed into the waste vial W1.

(2) From second reagent vial R2: With the second micro pump P2, pumping 2.5M sodium acetate 1.5 ml into GA-68-DOTATATE reactor G1, heating up to 95 degree C., and, after two minutes, conveying into C-18 reversed phase chromatography column C1 for purification and being collected in collection vial V1.

(3) From third reagent vial R3: With the third pump P3, conveying DI water 2 ml from the third reagent vial R3 through GA-68-DOTATATE reactor G1 and C-18 reversed phase chromatography column C1 into the collection vial V2, and the other 6 ml DI water being fed directly into C-18 reversed phase chromatography column C1 and then collected in the collection vial V3.

(4) From fourth reagent vial R4: With the fourth pump P4, pumping the 0.6 ml absolute ethanol into GA-68-DOTATATE reactor G1, and through C-18 reversed phase chromatography column C1 for purification, then collected in the fourth collection vial V4, and the other 0.5 ml absolute ethanol fed through C-18 reversed phase chromatography column C1, then the purified GA-68-DOTATATE collected in the fifth collection vial V5 as final product of the present invention.

Figure 4:
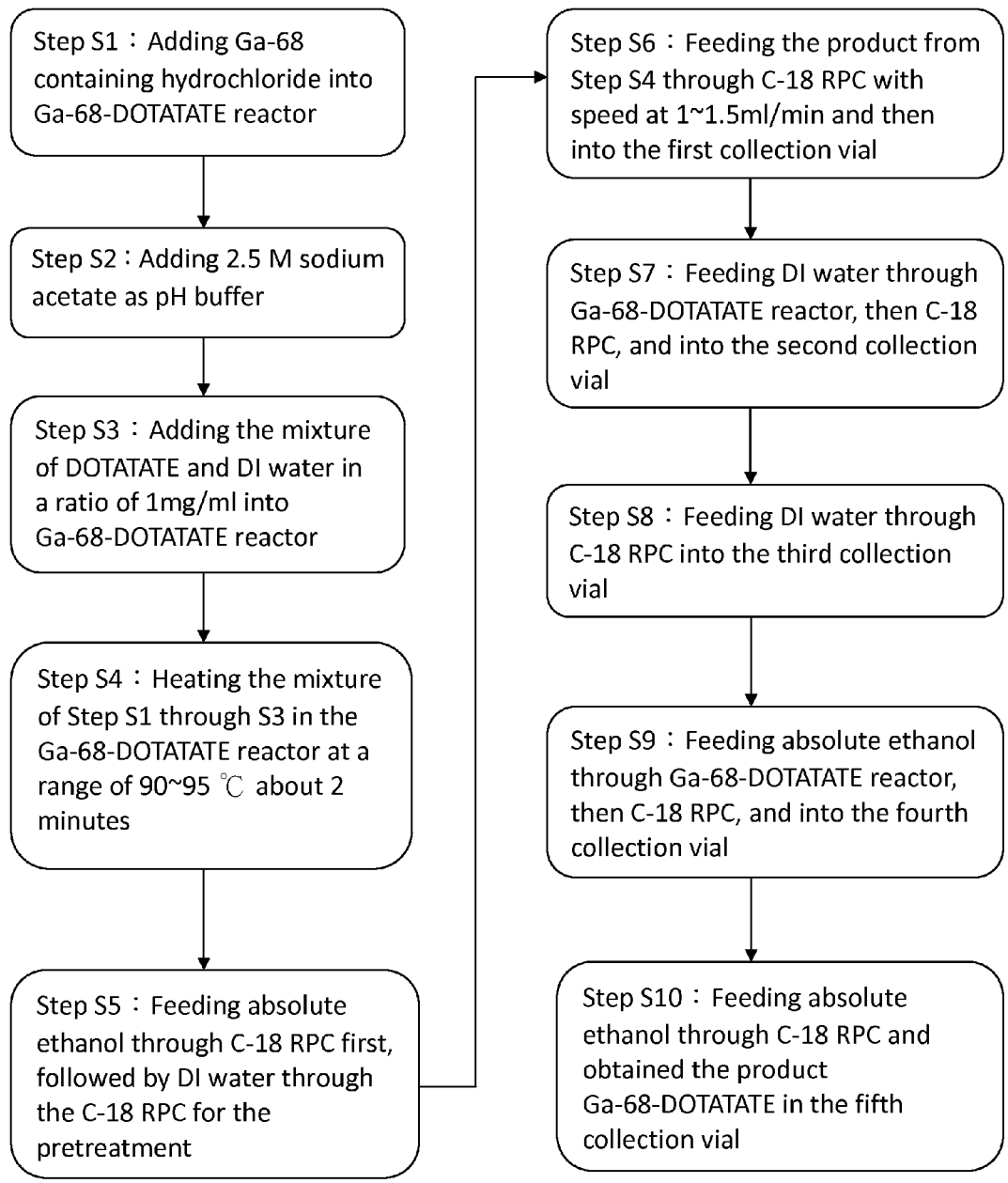
FIG. 4 is a flow diagram of the automatic synthesizer apparatus of the present invention for producing radiopharmaceutical tumor imaging agent Gallium-68-DOTATATE.

In the FIG. 4, the flow diagram of the automatic synthesizer apparatus of the present invention is shown for producing Gallium-68-DOTATATE, including steps:

Step S1: adding GA-68 containing 4 ml hydrochloride into GA-68-DOTATATE reactor, wherein the GA-68 containing hydrochloride is obtained by use of GA-68 containing 0.6M hydrochloride eluent washing in GA-68 Tin dioxide generator or 0.1M hydrochloride eluent washing in GA-68 Titanium dioxide and the radioactivity of GA-68 to be determined less than 630 MBq, the high impurity or redundant GA-68 radioactive liquid will be fed into waste vial W1.

Step S2: adding 2.5 M sodium acetate 1.5 ml as PH buffer.

Step S3: adding 50 μL of the mixture of DOTATATE and DI water in a ratio of 1 mg/ml into GA-68-DOTATATE reactor.

Step S4: heating the mixture of Step S1 through S3 in the GA-68-DOTATATE reactor at a range of 90~95 degree C. about two minutes for radioactive labeling.

Step S5: feeding absolute ethanol 4 ml through C-18 RPC C1 first, followed by DI water 2 ml through C-18 RPC C1 for the pretreatment.

Step S6: feeding the product from S4 through C-18 RPC C1 with speed at 1~1.5 ml/min and then into the first collection vial V1.

Step S7: feeding DI water through GA-68-DOTATATE reactor, then C-18 RPC, and into the second collection vial V2.

Step S8: feeding 6 ml DI water through C-18 RPC into the third collection vial V3.

Step S9: feeding absolute ethanol through GA-68-DOTATATE reactor G1, then C-18 RPC, and into the fourth collection vial V4.

Step S10: feeding absolute ethanol through C-18 RPC and obtained the product 0.5 ml GA-68-DOTATATE in the fifth collection vial V5.

Figure 5:
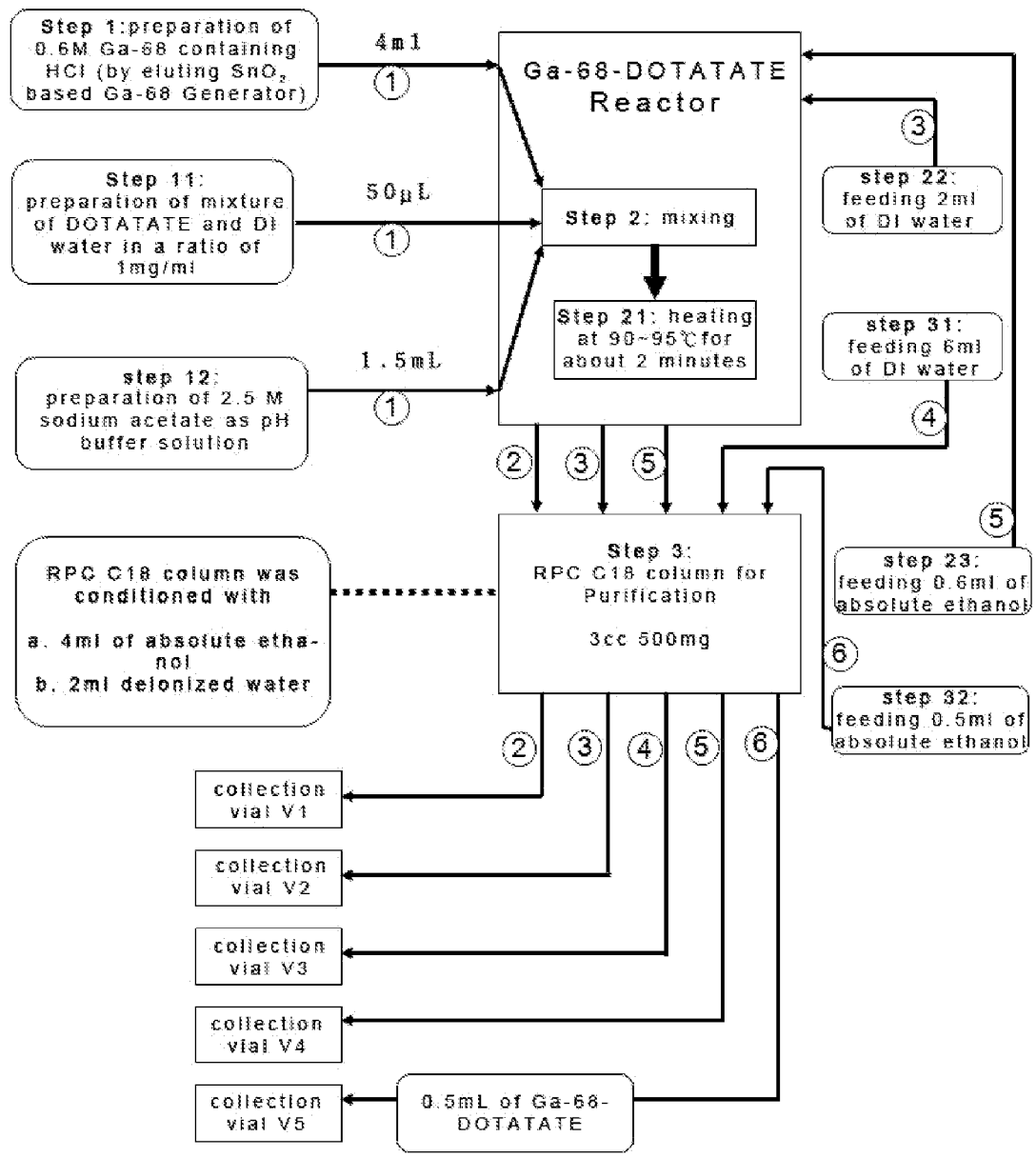
FIG. 5 is example one of embodiment of the automatic synthesizer apparatus of the present invention for producing radiopharmaceutical tumor imaging agent Gallium-68-DOTATATE.

In the FIG. 5, the example one of embodiment of the automatic synthesizer apparatus of the present invention is described for producing Gallium-68-DOTATATE, including six stages:

In Stage 1, including (1) step 1: preparation of 0.6M GA-68 containing hydrochloride 4 ml, obtained by use of GA-68 containing 0.6M hydrochloride eluent washing through Tin dioxide based Ga-68 generator, and the radioactivity to be determined larger than 630 MBq; (2) step 11: preparation of 50 µL mixture of DOTATATE and DI water in a ratio of 1 mg/ml; (3) step 12: preparation of 2.5 M sodium acetate 1.5 ml as pH buffer.

In Stage 2, including (1) step 2: mixing the products obtained from step 1, 11, 12 in GA-68-DOTATATE reactor; (2) step 21: heating the mixture product from step 2 at 90~95 degree C. about two minutes; (3) step 3: feeding absolute ethanol 4 ml, then DI water 2 ml through 3 cc, 500 mg C-18 RPC for pretreatment, and feeding the product from step 21 through C-18 RPC into collection vial V1;

In Stage 3, including (1) step 22: feeding 2 ml of DI water through GA-68-DOTATATE reactor following the completion of Stage 2, then through C-18 RPC, and into the second collection V2.

In Stage 4, including (1) step 31: feeding 6 ml DI water through C-18 RPC following the completion of Stage 3, and into the third collection vial V3.

In Stage 5, including (1) step 23: feeding 0.6 ml absolute ethanol through GA-68-DOTATATE reactor following the completion of Stage 4, then C-18 RPC, and into the fourth collection vial V4.

In Stage 6, including (1) step 32: feeding 0.5 ml absolute ethanol through C-18 RPC after completion of Stage 5, and finally into the fifth collection vial V5 to obtain the product of 0.5 ml GA-68-DOTATATE.

Figure 6:
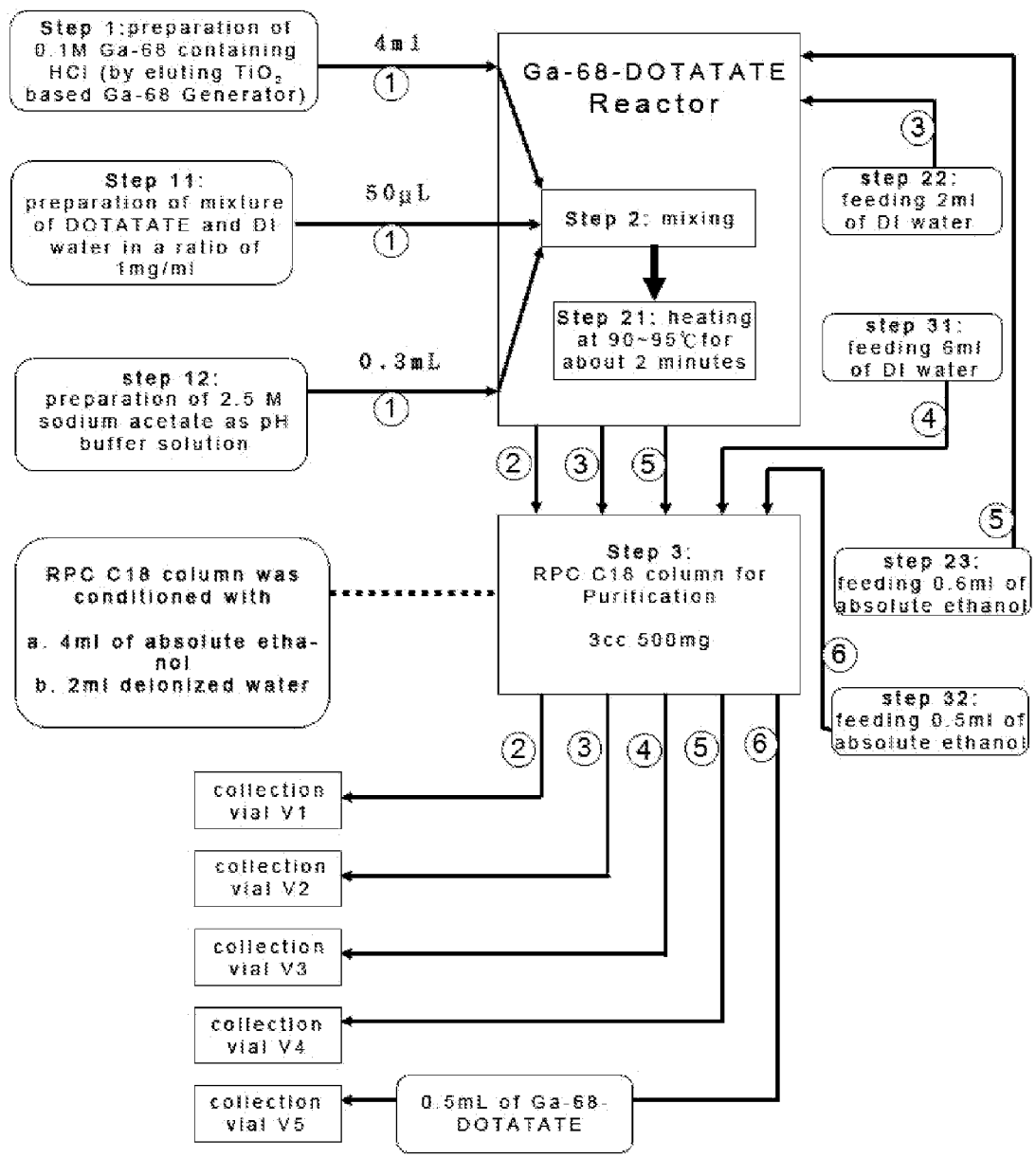
FIG. 6 is example two of embodiment of the automatic synthesizer apparatus of the present invention for producing radiopharmaceutical tumor imaging agent Gallium-68-DOTATATE.

FIG. 6 is example two of embodiment of the automatic synthesizer apparatus of the present invention for producing Gallium-68-DOTATATE, including 6 stages:

In the Stage 1, including (1) step 1: preparation of 0.1M GA-68 containing 4 ml hydrochloride, obtained by use of 0.1M GA-68 containing hydrochloride eluent washing through Titanium dioxide based Ga-68 generator, and the radioactivity to be measured at value larger than 630 MBq; (2) step 11: preparation of 50 µL mixture of 50 µg DOTATATE and DI water in a ratio of 1 mg/ml; (3) step 12: preparation of 2.5 M sodium acetate 0.3 ml as PH buffer.

In Stage 2, including (1) step 2: mixing the products obtained in step 1, 11, 12 from Stage 1 in GA-68-DOTATATE reactor; (2) step 21: heating the mixture product from step 2 at 90~95 degree C. about two minutes; (3) step 3: feeding absolute ethanol 4 ml, then DI water 2 ml through 3 cc, 500 mg C-18 RPC for pretreatment, and feeding the product from step 21 through C-18 RPC into collection vial V1;

In Stage 3, including (1) step 22: feeding 2 ml DI water through GA-68-DOTATATE reactor following the completion of Stage 2, then through C-18 RPC, and into the second collection V2.

In Stage 4, including (1) step 31: feeding 6 ml DI water through C-18 RPC following the completion of Stage 3, and into the third collection vial V3.

In Stage 5, including (1) step 23: feeding 0.6 ml absolute ethanol through GA-68-DOTATATE reactor following the completion of Stage 4, then C-18 RPC, and into the fourth collection vial V4.

In Stage 6, including (1) step 32: feeding 0.5 ml absolute ethanol through C-18 RPC after completion of Stage 5, and finally into the fifth collection vial V5 to obtain the product of 0.5 ml GA-68-DOTATATE.

From the above mentioned description, the automatic synthesizer apparatus of the present invention for producing radiopharmaceutical tumor imaging agent Gallium-68-DOTATATE has advantages including improving yield of production, simplifying the process of control, and solving problems encountered with bulk software programs associated with the conventional equipments.

The foregoing invention has been described in detail by way of illustration and example for purposes of clarity and understanding. It will be apparent to those of ordinary skill in the art that variations, changes, modifications and alterations may be applied to the compositions and/or methods described herein without departing from the true spirit, concept and scope of the invention.

What is claimed is:

1. An automatic synthesizer apparatus for producing radiopharmaceutical tumor imaging agent Gallium-68-DOTATATE, consisting of:
   first reagent vial being connected to first micro pump, and connected to Gallium-68-DOTATATE reactor and a waste vial through first solenoid valve and connected to C-18 reversed phase chromatography through fifth micro pump,
   second reagent vial being connected to C-18 reversed phase chromatography through second micro pump and connected to C-18 reversed phase chromatography through fifth micro pump,
   third reagent vial being connected to third micro pump, and connected to Gallium-68-DOTATATE reactor and C-18 reversed phase chromatography through second solenoid valve, respectively,
   fourth reagent vial being connected to micro pump and connected to Gallium-68-DOTATATE reactor and C-18 reversed phase chromatography through four solenoid valve, respectively,
   wherein the C-18 reversed phase chromatography is further connected to fifth and seventh solenoid valve, respectively, through sixth solenoid valve, in which the fifth solenoid valve is connected to fourth solenoid valve and third collection vial, in which the four solenoid valve is connected to first and second collection vial, respectively,
   wherein the seventh solenoid valve is connected to fourth collection vial and eighth solenoid valve, in which the eighth solenoid valve is connected to fifth and a spare collection vial, respectively.

2. The automatic synthesizer apparatus as claimed in claim 1, wherein the first solenoid valve controls the access to the first reagent gallium-68 radioactive solution to the Gallium-68-DOTATATE reactor, wherein when radioactivity of the first reagent gallium-68 exceeds 630 MBq or a volume of the first reagent gallium-68 is redundant in the Gallium-68-DOTATATE reactor, the first solenoid valve will let the reagent gallium-68 flow into a waste vial;
   the second solenoid valve controls flow of the DI water into the Gallium-68-DOTATATE reactor and the C-18 reversed phase chromatography column;

the third solenoid valve controls flow of the absolute ethanol into the Gallium-68-DOTATATE reactor and the C-18 reversed phase chromatography column;

the fourth solenoid valve controls flow of hydrochloric acid, sodium acetate and DOTATATE with gallium-68 nuclide after being mixed and heated in the Gallium-68-DOTATATE reactor and passing through C-18 reversed phase chromatography column before being collected in the first collection vial, or controls flow of the DI water eluent into the second collection vial;

the fifth solenoid valve control flowing of the DI water eluent into the third collection vial;

the sixth solenoid valve controls flow of solution after passing through C-18 reversed phase chromatography column to the fifth solenoid valve or the seventh solenoid valve;

the seventh solenoid valve controls flow of the absolute ethanol eluent into the fourth collection vial and through the eighth solenoid valve into the fifth collect vials, and the eighth solenoid valve controls flow of absolute ethanol eluent to the fifth collect vials or into the reserve vial.

3. The automatic synthesizer apparatus as claimed in claim 1, wherein the first reagent vial contains with hydrochloride with gallium-68 nuclides; the second reagent vial contains with sodium acetate; the third reagent vial contains a DOTATATE solution or DI water alternatively; and the fourth reagent vial contains absolute ethanol.

4. A method of using the automatic synthesizer apparatus of claim 1 for producing radiopharmaceutical tumor imaging agent Gallium-68-DOTATATE, comprising steps:

S1: adding Gallium-68 containing hydrochloride into Gallium-68-DOTATATE reactor, wherein the radioactivity of Gallium-68 is measured and kept to be less than 630 MBq, and Gallium-68 liquid with exceeding radioactive will be conveyed into a waste vial;

S2: adding 2.5 M sodium acetate as PH buffer;

S3: adding 50 µL of the mixture of DOTATATE and DI water in a ratio of 1 mg/ml into Gallium-68-DOTATATE reactor;

S4: heating the mixture of Step S1 through S3 in the Gallium-68-DOTATATE reactor at a range of 90~95 degree C. about two minutes for radioactive labeling;

S5: feeding absolute ethanol 4 ml through C-18 RPC C1 first, followed by DI water 2 ml through C-18 RPC C1 for the pretreatment;

S6: feeding the product from S4 through C-18 RPC C1 with speed at 1~1.5 ml/min and then into the first collection vial V1;

S7: feeding 2 ml DI water through Gallium-68-DOTATATE reactor, C-18 RPC, and then into the second collection vial V2;

S8: feeding 6 ml DI water through C-18 RPC into the third collection vial V3;

S9: feeding absolute ethanol 0.6 ml through Gallium-68-DOTATATE reactor, C-18 RPC, and then into the fourth collection vial V4;

S10: feeding absolute ethanol through C-18 RPC and obtaining the product of 0.5 ml Gallium-68-DOTATATE in the fifth collection vial V5.

* * * * *